US006965288B2

(12) United States Patent
Terentiev

(10) Patent No.: US 6,965,288 B2
(45) Date of Patent: Nov. 15, 2005

(54) PUMPING OR MIXING SYSTEM USING A LEVITATING MAGNETIC ELEMENT

(75) Inventor: Alexandre N. Terentiev, Lexington, KY (US)

(73) Assignee: University of Kentucky Research Foundation, Lexington, KY (US)

(*) Notice: Subject to any disclaimer, the term of this patent is extended or adjusted under 35 U.S.C. 154(b) by 521 days.

(21) Appl. No.: 10/078,229

(22) Filed: Feb. 19, 2002

(65) Prior Publication Data

US 2002/0082173 A1    Jun. 27, 2002

Related U.S. Application Data

(63) Continuation of application No. 09/460,600, filed on Dec. 14, 1999, now Pat. No. 6,416,215.

(60) Provisional application No. 60/114,655, filed on Jan. 4, 1999.

(51) Int. Cl.[7] .......................... H01F 6/20; B01F 13/08
(52) U.S. Cl. ...................... 335/216; 62/51.1; 505/879; 505/892; 366/273; 366/274; 417/420

(58) Field of Search .................. 366/273, 274; 505/166, 879, 892; 417/420; 335/216; 62/51.1

(56) References Cited

U.S. PATENT DOCUMENTS

| 4,615,662 | A |   | 10/1986 | Laing |
| 5,049,134 | A |   | 9/1991  | Golding et al. |
| 5,177,054 | A |   | 1/1993  | Lloyd et al. |
| 5,331,819 | A | * | 7/1994  | Matsuda et al. ............. 62/51.1 |
| 5,774,032 | A | * | 6/1998  | Herd et al. .................. 335/216 |
| 6,033,377 | A |   | 3/2000  | Rasmussen et al. |

FOREIGN PATENT DOCUMENTS

| JP | 02403263 | 12/1990 |
| JP | 03200201 | 2/1993 |

* cited by examiner

Primary Examiner—Ramon M. Barrera
(74) Attorney, Agent, or Firm—King & Schickli, PLLC

(57) ABSTRACT

A system capable of pumping or mixing fluids using a rotating magnetic element or bearing levitated by a cold superconducting element is disclosed.

24 Claims, 5 Drawing Sheets

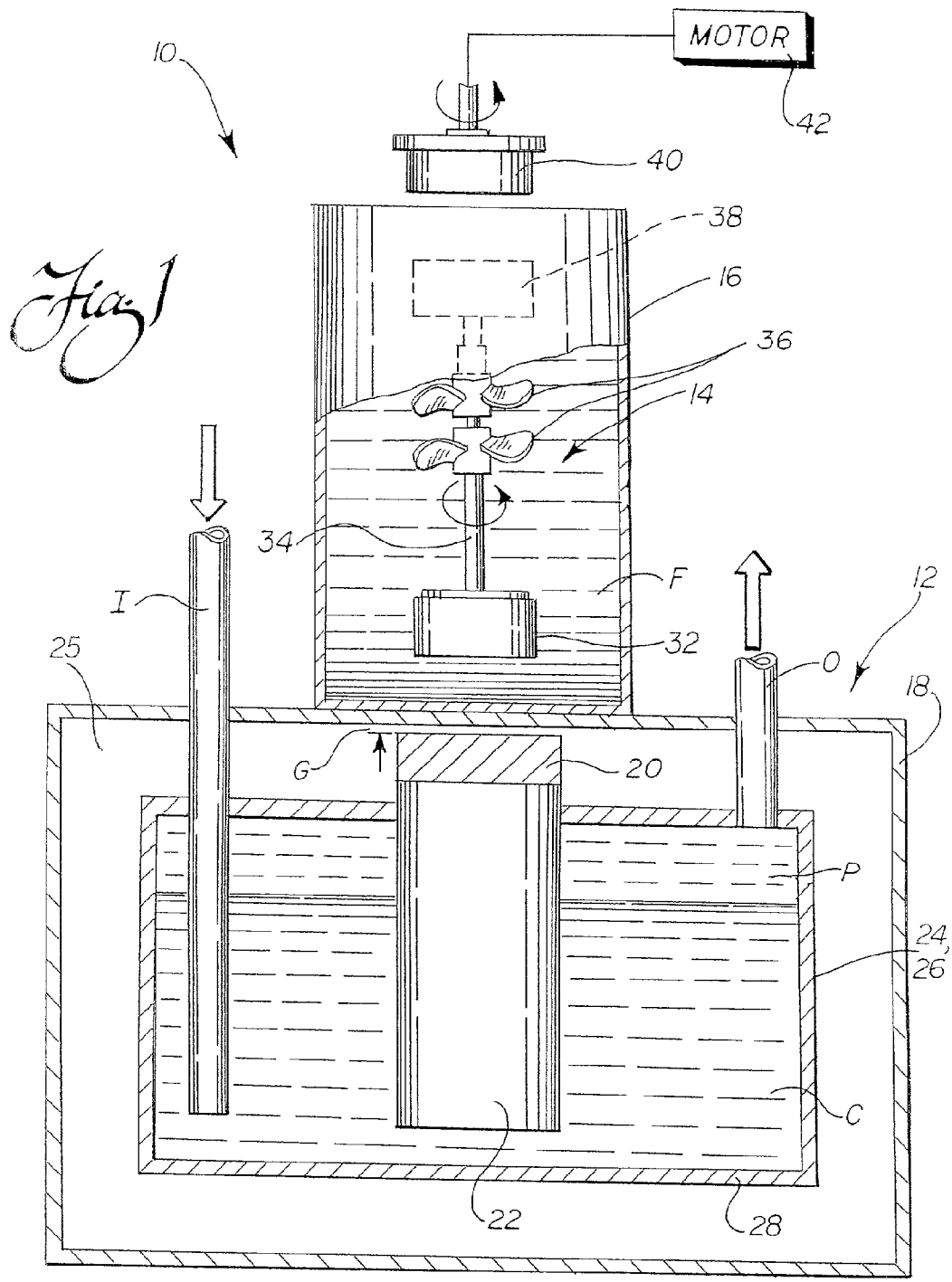

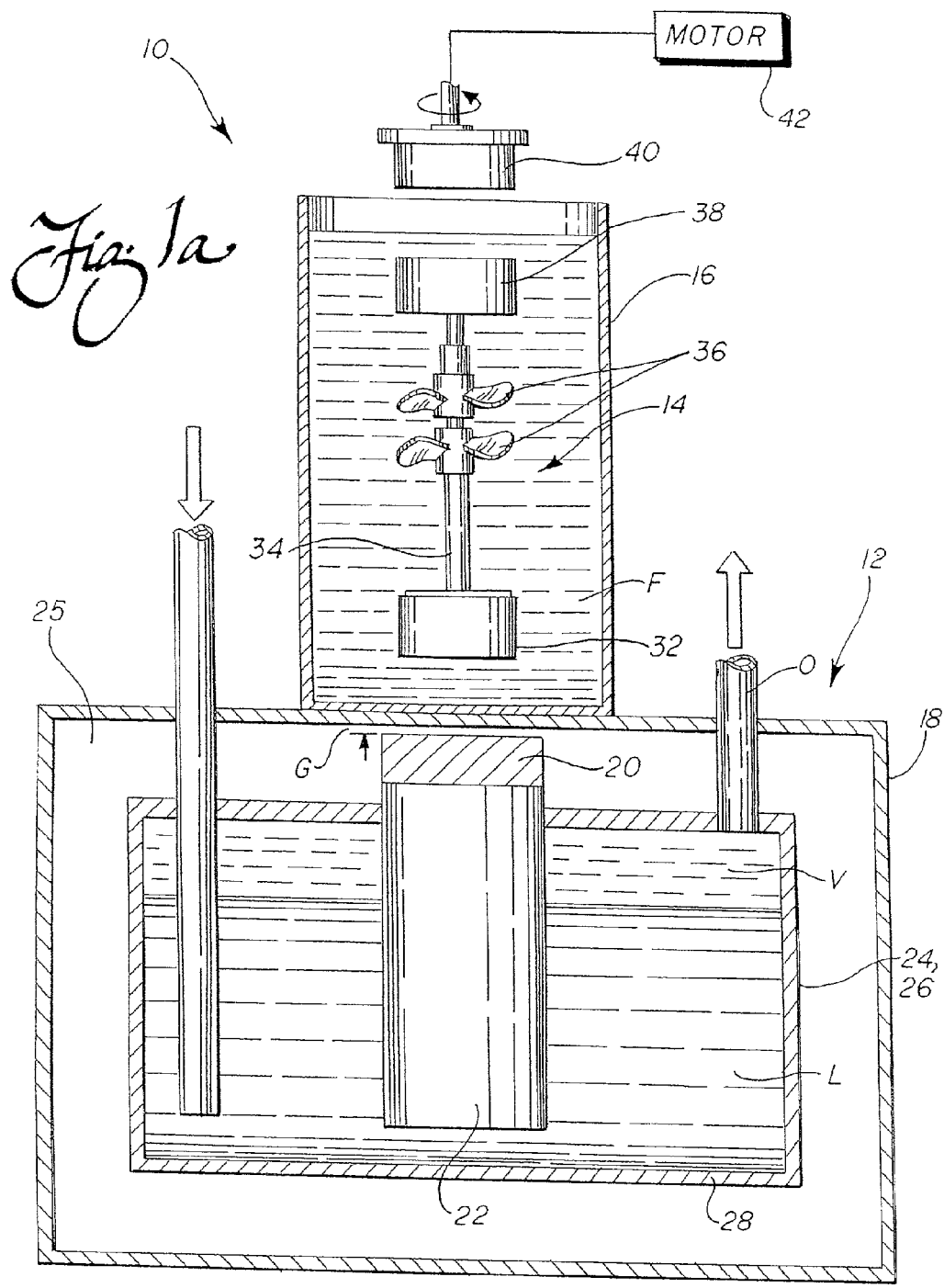

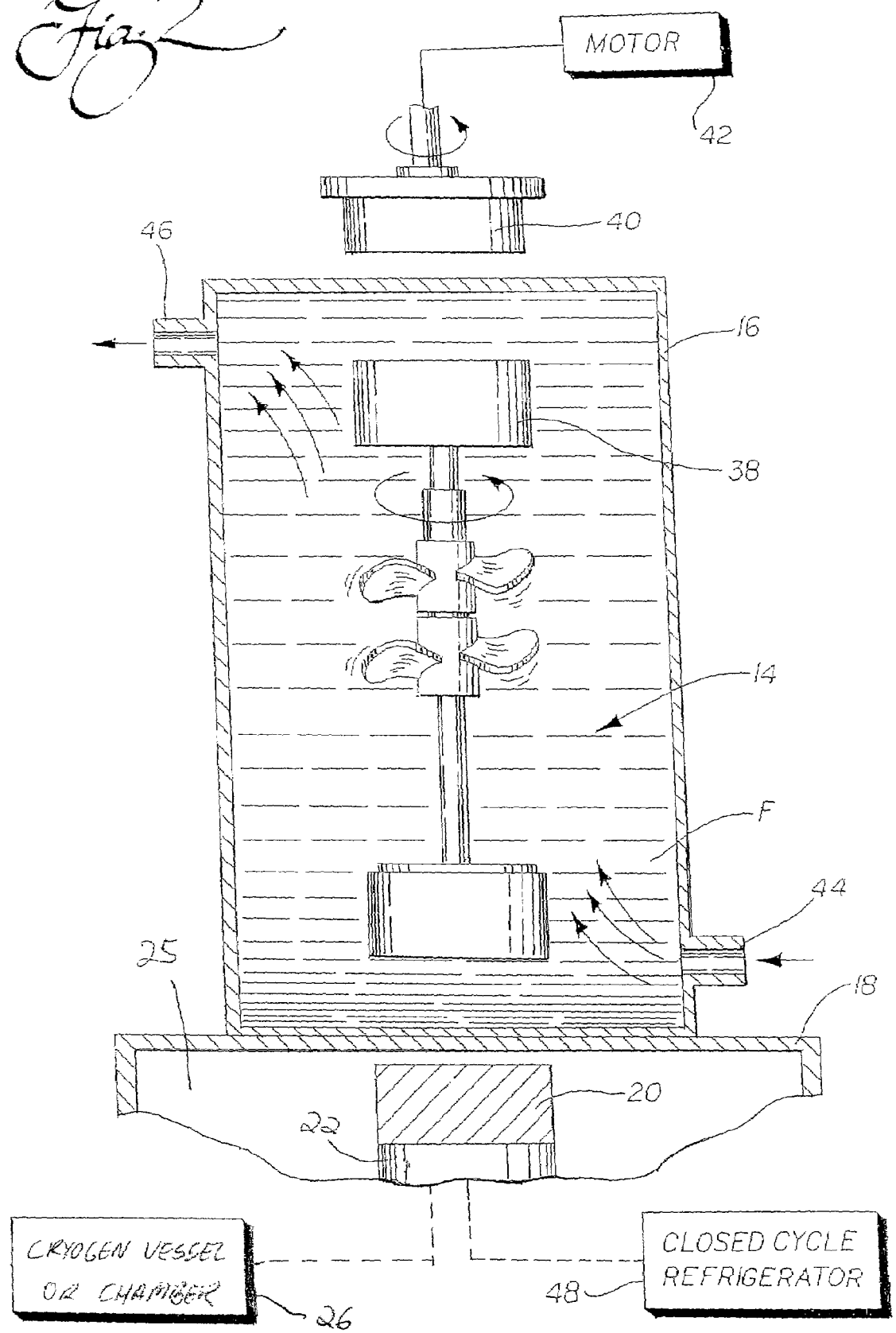

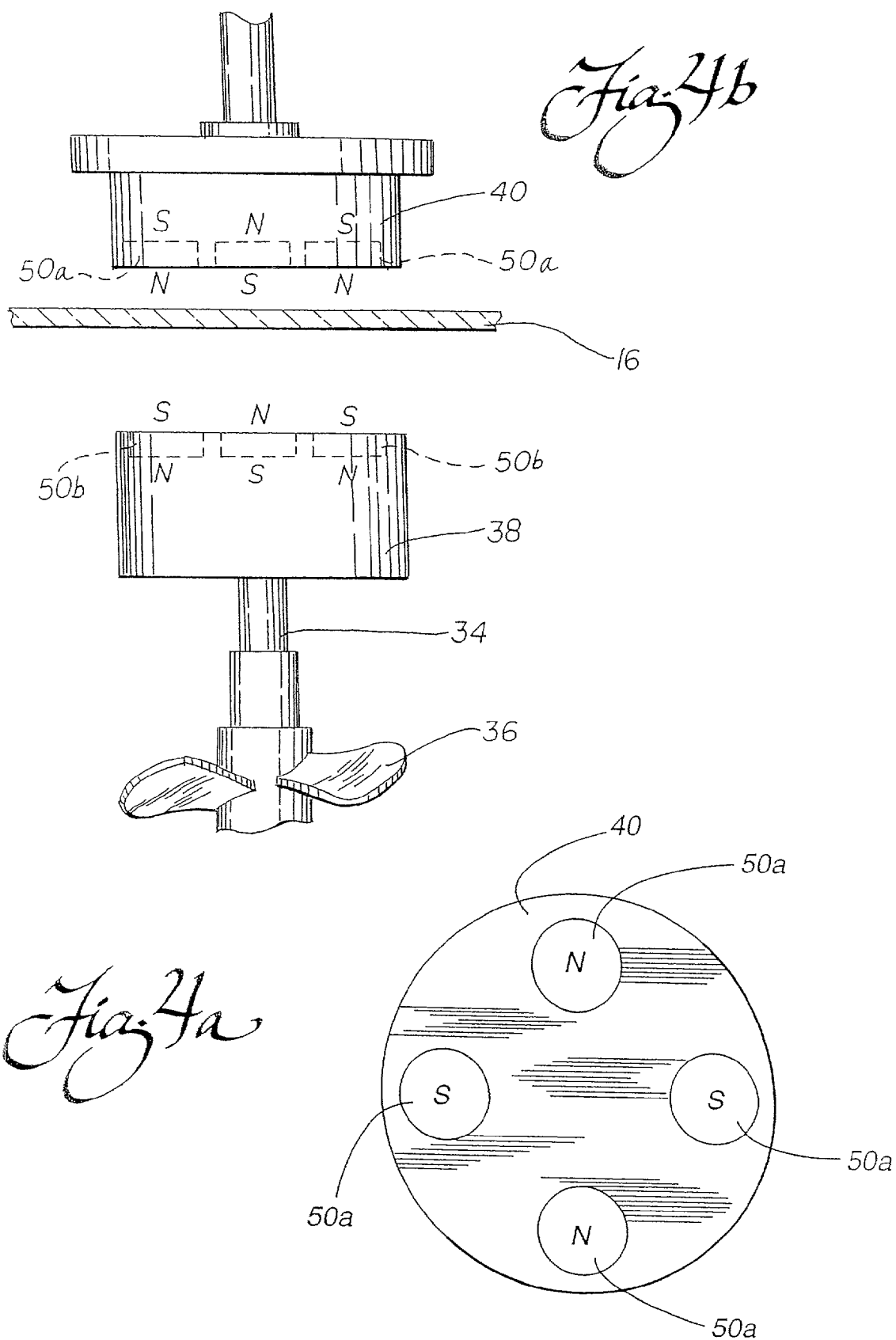

PUMPING OR MIXING SYSTEM USING A LEVITATING MAGNETIC ELEMENT

This application is a continuation of the filing date of U.S. patent application Ser. No. 09/460,600, entitled "Pumping or Mixing System Using a Levitating Magnetic Element," now U.S. Pat. No.6,416,215, the disclosure of which is incorporated herein by reference. This application claims benefit of Provisional 60/144,655 filed Jan. 4, 1999.

TECHNICAL FIELD

The present invention relates to systems for levitating magnetic elements for mixing or pumping fluids or the like and, more particularly, to a system that is capable of pumping or mixing a fluid using a rotating magnetic element or bearing that levitates above a cold superconducting element positioned in a cryostat.

BACKGROUND OF THE INVENTION

Most pharmaceutical solutions and suspensions manufactured on an industrial scale require highly controlled, thorough mixing to achieve a satisfactory yield and a uniform distribution of ingredients in the final product. Agitator tanks are frequently used to complete the mixing process, but a better degree of mixing is normally achieved using a mechanical stirrer or impeller (e.g., a set of mixing blades attached to a steel rod). Typically, the mechanical stirrer or impeller is simply lowered into the fluid through an opening in the top of the vessel and rotated by an external motor to create the desired mixing action.

One significant limitation or shortcoming of such an arrangement is the danger of contamination or leakage during mixing. The rod carrying the mixing blades or impeller is typically introduced into the vessel through a dynamic seal or bearing. This opening provides an opportunity for bacteria or other contaminants to enter, which of course can lead to the degradation of the product. A corresponding danger of environmental contamination exists in applications involving hazardous or toxic fluids, or suspensions of pathogenic organisms, since dynamic seals or bearings are prone to leakage. Cleanup and sterilization are also made difficult by the dynamic bearings or seals, since these structures typically include folds and crevices that are difficult to reach. Since these problems are faced by all manufacturers of sterile solutions, pharmaceuticals, or the like, the U.S. Food and Drug Administration (FDA) has consequently promulgated strict processing requirements for such fluids, and especially those slated for intravenous use.

Recently, there has also been an extraordinary increase in the use of biosynthetic pathways in the production of pharmaceutical materials, but problems plague those involved in this rapidly advancing industry. The primary problem is that suspensions of genetically altered bacterial cells frequently used to produce protein pharmaceuticals (insulin is a well-known example) require gentle mixing to circulate nutrients. If overly vigorous mixing or contact between the impeller and the vessel wall occurs, the resultant forces and shear stresses may damage or destroy a significant fraction of the cells, as well as protein molecules that are sensitive to shear stresses. This not only reduces the beneficial yield of the process, but also creates deleterious debris in the fluid suspension that requires further processing to remove.

In an effort to overcome this problem, others have proposed alternative mixing technologies. The most common proposal for stirring fluids under sterile conditions is to use a rotating, permanent magnet bar covered by an inert layer of TEFLON, glass, or the like. The magnetic bar is placed on the bottom of the agitator vessel and rotated by a driving magnet positioned external to the vessel. Of course, the use of such an externally driven magnetic bar avoids the need for a dynamic bearing, seal or other opening in the vessel. Therefore, a completely enclosed system may be provided. This of course prevents leakage and the potential for contamination created by hazardous materials (e.g., cytotoxic agents, solvents with low flash points, blood products, etc.), eases clean up, and allows for the desirable sterile interior environment to be maintained.

However, several well-recognized drawbacks are associated with this mixing technology, making it unacceptable for use in many applications. For example, the driving magnet produces not only torque on the stirring magnetic bar, but also an attractive axial thrust force tending to drive the bar into contact with the bottom wall of the vessel. This of course generates substantial friction at the interface between the bar and the bottom wall of the vessel. This uncontrolled friction generates unwanted heat and may also introduce an undesirable shear stress in the fluid. Consequently, fragile biological molecules, such as proteins and living cells that are highly sensitive to temperature and shear stress, are easily damaged during the mixing process, and the resultant debris may contaminate the product. Moreover, the magnetic bar stirrer does not generate the level of circulation provided by an impeller, and thus cannot be scaled up to provide effective mixing throughout the entire volume of large agitation tanks of the type preferred in commercial production operations.

In yet another effort to eliminate the need for dynamic bearings or shaft seals, some have proposed mixing vessels having external magnets that remotely couple a mixing impeller mechanically supported by a roller bearing assembly or the like to a motor located externally to the vessel. A typical magnetic coupler consists of a drive magnet attached to the motor and a stirring magnet carrying an impeller. Similar to the magnetic bar technology described above, the driver and stirrer magnets are kept in close proximity to ensure that the coupling between the two is strong enough to provide sufficient torque. An example of one such proposal is found in U.S. Pat. No. 5,470,152 to Rains.

As described above, the high torque generated can drive the impeller into the walls of the vessel creating significant friction. By strategically positioning the roller bearings inside the vessel, the effects of friction between the impeller and the vessel wall can be substantially reduced. Of course, high stresses at the interfaces between the ball bearings and the vessel wall or impeller assembly result in a grinding of the mixing proteins and living cells, and loss of yield. Further, the bearings are frequently sensitive to corrosive reactions with water-based solutions and other media and will eventually deteriorate, resulting in frictional losses which slow the impeller and reduce the mixing action and eventually also lead to undesirable contamination of the product. Bearings also add to the cleanup problems.

In an effort to address and overcome the limitations described above, still others have proposed levitated bearings designed to reduce the deleterious effects of friction resulting from magnetically coupled mixers. By using a specially configured magnetic coupler to maintain only a repulsive levitation force in the vertical direction, the large thrust force between the stirring and driving magnets can be eliminated, along with the resultant shear stress and frictional heating. An example of one such arrangement is shown in U.S. Pat. No. 5,478,149 to Quigg.

However, one limitation remaining from this approach is that only magnet-magnet interactions provide the levitation. This leads to intrinsically unstable systems that produce the desired levitation in the vertical direction, but are unable to control side-to-side movement. As a result, external contact bearings in the form of bearing rings are necessary to laterally stabilize the impeller. Although this "partial" levitation reduces the friction between the impeller and the vessel walls, it does not totally eliminate the drawbacks of the magnetically coupled, roller bearing mixers previously mentioned.

In an effort to eliminate the need for contact or other types of mechanical roller bearings, complex feedback control has been proposed to stabilize the impeller. Typical arrangements use electromagnets positioned alongside the levitating magnet. However, the high power level required to attain only sub-millimeter separations between the levitating magnet and the stabilizing magnets constitutes a major disadvantage of this approach. Furthermore, this solution is quite complex, since the stabilizing magnets must be actively monitored and precisely controlled by complex computer-implemented software routines to achieve even a moderate degree of stability. As a consequence of this complexity and the associated maintenance expense, this ostensible solution has not been accepted in the commercial arena, and it is doubtful that it can be successfully scaled up for use in mixing industrial or commercial scale process volumes.

Thus, a need is identified for an improved system having a levitating magnetic element or bearing for mixing or pumping fluids, and especially ultra-pure, hazardous, or delicate fluid solutions or suspensions. The system would preferably employ a magnetic pumping or mixing element or bearing that carries an impeller and levitates in a stable fashion to avoid contact with the bottom or side walls of the vessel. Since the pumping or mixing element or bearing would levitate in the fluid, no mixing rod or other structure penetrating the mixing vessel would be necessary, thus eliminating the need for dynamic bearings or seals and all potentially deleterious effects associated therewith. Since penetration is unnecessary, the vessel could be completely sealed prior to mixing to avoid the potential for contamination and reduce the potential for exposure in the case of hazardous or biological fluids, such as contaminated blood or the like. The vessel and magnetic pumping or mixing element/bearing could also be made of disposable materials and discarded after each use, which would eliminate the need for cleaning or sterilization. The absence of a mixing or stirring rod penetrating through the vessel would also allow a slowly rotating impeller to be held at an off-axis position in a sealed vessel, thus making it possible to independently rotate the vessel about its central axis to achieve very gentle, yet thorough, mixing.

The use of superconductivity to provide the desired levitation would be possible by thermally isolating and separating the superconducting element from the magnetic pumping or mixing element or bearing and providing a separate, substantially isolated cooling source. This combined thermal isolation and separation would avoid creating any significant cooling in the vessel, magnetic bearing or the fluid being mixed or pumped. Overall, the proposed system would have superior characteristics over existing mixing or pumping technologies in sterility, mixing quality, safety and reliability, and would be readily adaptable for use in larger, industrial scale operations.

SUMMARY OF THE INVENTION

In accordance with a first aspect of the invention, an apparatus for the intended use of levitating a magnetic element, such as a rotatable pumping or mixing element held in a vessel capable of receiving or holding a fluid, is disclosed. The apparatus comprises: (1) a superconducting element capable of being placed in a superconducting state in accordance with a field cooling protocol for levitating the magnetic element; and (2) a structure including a wall defining a first chamber in which the superconducting element is positioned, said first chamber thermally isolating the superconducting element from the first wall, a second chamber including a cooling source, and a thermal link extending between the superconducting element positioned in said first chamber and the cooling source in said second chamber.

Preferably, the first chamber is evacuated or insulated to minimize thermal transfer to the first wall and provide the desired thermal isolation. Specifically, the first chamber may be evacuated to a vacuum pressure of at least $10^{-3}$ torr. The superconducting element is preferably a high temperature superconducting element and, most preferably, one fabricated of melt-textured Yttrium-Barium Copper Oxide (YBCO). By way of the thermal link, the cooling source maintains the superconducting element at a temperature of between 4.2 to 130 Kelvin and, most preferably, at a temperature of between approximately 77 to 78 Kelvin.

In one embodiment, the structure is a cryostat, the wall is the outer wall of the cryostat, the second chamber is positioned in said first chamber, and the cooling source is a liquid cryogen. Also, the thermal link is a rod including an engagement surface that is in contact with the entire area of an adjacent surface of the superconducting element to maximize thermal transfer. A gap is also provided between said superconducting element and an inner surface of the wall of approximately 0.01 to 5 millimeters.

In an alternative embodiment, a refrigerator capable of maintaining the superconducting element in a superconducting state is also provided. The refrigerator may serve as a primary cooling source, while the second chamber is a back-up or reserve cooling source.

In accordance with a second aspect of the invention, an apparatus for the intended use of supplying a levitating force for a magnetic element, such as a rotatable pumping or mixing element held in a vessel capable of receiving or holding a fluid, is disclosed. The apparatus comprises a superconducting element capable of being placed in a superconducting state in accordance with a field cooling protocol for levitating the magnetic element and a structure including a wall defining a chamber in which the superconducting element is positioned. The chamber thermally isolates the superconducting element from the outer wall, and a refrigerator is thermally linked to the superconducting element.

In one embodiment, the chamber in which the superconducting element is positioned is evacuated or insulated to minimize thermal transfer to the wall and provide the desired thermal isolation. Preferably, the space is evacuated to a vacuum pressure of at least $10^{-3}$ torr. The superconducting element is preferably a high temperature superconducting element and most preferably one fabricated of melt-textured Yttrium-Barium Copper Oxide (YBCO). The refrigerator preferably maintains the superconducting element at a temperature of between 4.2 to 130 Kelvin and, most preferably, at a temperature of between approximately 77 to 78 Kelvin.

The thermal link may be provided by a rod extending between the superconducting element and the refrigerator.

The rod may include an engagement surface that is in contact with the entire area of an adjacent surface of the superconducting element to maximize thermal transfer. Preferably, the gap provided between the superconducting element and an inner surface of the wall is approximately 0.01 to 5 millimeters.

In an alternate embodiment, the apparatus may include a second structure capable of holding a liquid cryogen in contact with the thermal link. The second structure may serve as a backup or reserve cooling source for the superconducting element, in case the refrigerator fails or there is a power outage.

In accordance with a third aspect of the invention, an apparatus for the intended use of supplying a levitating force for a magnetic element is disclosed. The apparatus comprises a superconducting element capable of being placed in a superconducting state in accordance with a field cooling protocol for levitating the magnetic element. A structure includes a wall defining a first chamber in which the superconducting element is positioned and a second chamber. The first chamber is evacuated or insulated for thermally isolating the superconducting element from the wall. A cooling source is provided selected from the group consisting of: (a) a liquid cryogen held in the second chamber in said structure; and (b) a refrigerator. A link is also provided for thermally linking the superconducting element to the cooling source.

The link is preferably a rod extending between the cooling source and the superconducting element. The rod may have an engagement surface that is in contact with the entire area of an adjacent surface of the superconducting element to maximize thermal transfer. Preferably, the refrigerator is a closed-cycle refrigerator. In an alternative embodiment, the second chamber holding the liquid cryogen and the refrigerator may be provided. A method for levitating a rotatable magnetic pumping or mixing element held in a vessel capable of receiving or holding a fluid using the apparatus is also disclosed.

BRIEF DESCRIPTION OF THE DRAWINGS

The accompanying drawings incorporated in and forming a part of the specification illustrate several aspects of the present invention and, together with the description, serve to explain the principles of the invention. In the drawings:

FIG. 1 is a partially cross-sectional, partially cutaway, partially schematic view of one embodiment of the system of the present invention wherein the levitating magnetic bearing is rotated by an external drive magnet to mix a fluid in a vessel and the cooling source is a separate cooling chamber in a cryostat holding a cryogen;

FIG. 1a is a partially cross-sectional, partially cutaway, partially schematic view of one embodiment of the system of the present invention wherein the levitating magnetic element or bearing is rotated by an external drive magnet to mix a fluid in a vessel having a sealable opening at the top and a closed bottom with no pre-defined outlet and the cooling source is a separate cooling chamber in a cryostat holding a cryogen;

FIG. 2 is an enlarged cross-sectional, partially cutaway, partially schematic view of a second embodiment wherein the rotating, levitating magnetic bearing is used to pump a fluid through a vessel resting atop a housing for the superconducting element and the cooling source is a closed cycle refrigerator;

FIG. 4a is a bottom view of the drive magnet used in situations where exceptional rotational stability of the magnetic bearing of the preferred embodiment is required; and FIG. 4b is a partially cross-sectional, partially cutaway side view of the system showing the drive magnet of FIG. 4a magnetically coupled to a similarly constructed second permanent magnet forming a part of the magnetic bearing.

Figure 3:
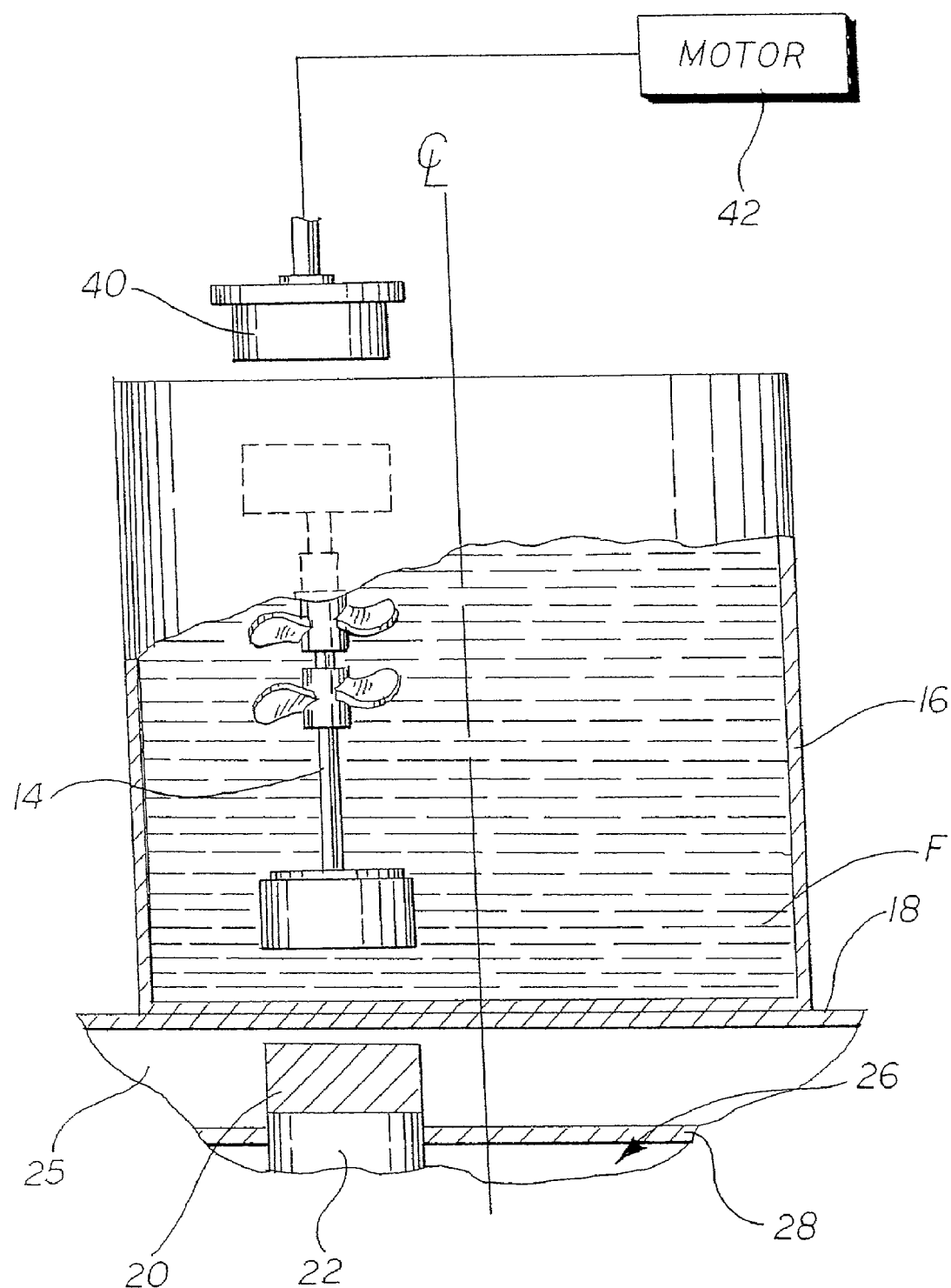
FIG. 3 is a partially cross-sectional, partially cutaway, partially schematic view of the system of the first embodiment wherein the superconducting element, vessel, magnetic bearing, and drive magnet are axially aligned, but moved off-center relative to the vertical center axis of the vessel.

Reference will now be made in detail to the present preferred embodiment of the invention, an example of which is illustrated in the accompanying drawing.

DETAILED DESCRIPTION OF THE INVENTION

Reference is now made to FIG. 1, which shows a first embodiment of the mixing or pumping system 10. In this embodiment, a cryostat 12 is used as the cooling source for the superconductor that produces the desired levitation in a magnetic pumping or mixing element 14, which is shown for purposes of illustration as a magnetic bearing 14. The magnetic element or bearing 14 is placed in a vessel 16 positioned external to the cryostat 12, which may already contain a fluid F or may be filled after the bearing is in place. The vessel 16 is shown as cylindrical in shape and may have an open top (see FIG. 1a). Alternatively, it may be completely sealed from the ambient environment to avoid the potential for fluid contamination or leakage during mixing, or adapted to pump the fluid F from an inlet to an outlet in the vessel 16 (see FIG. 2). In any case, the vessel 16 may be fabricated of any material suitable for containing fluids, including glass, plastic, metal, or the like. Of course, the use of lightweight plastic or other high density polymers is particularly desirable if the vessel 16 is going to be discarded after mixing or pumping is complete, as set forth in more detail in the description that follows.

As illustrated, the vessel 16 rests atop the outer wall 18 of the cryostat 12. Preferably, this outer wall 18 is fabricated of non-magnetic stainless steel, but the use of other materials is of course possible, as long as the ability of the magnetic bearing 14 to levitate remains substantially unaffected. Positioned inside of the wall 18 is a superconducting element 20, which is supported by a rod 22 that provides the thermal link between the superconducting element 20 and a cooling source 24. The outer wall 18 of the cryostat 12 defines a chamber 25 that is preferably evacuated to thermally isolate the cold superconducting element 20 from the relatively warm vessel 16, magnetic bearing 14, and fluid F. Positioning of the superconducting element 20 in this vacuum chamber 25 is possible by virtue of the thermal link provided by the rod 22. The thermal isolation and separation provided by the chamber 25 allows for the superconducting element 20 to be placed in very close proximity to the outer wall 18 without affecting the temperature of the outer wall 18 or vessel 16. This allows the separation distance from the superconducting element 20 to the inner surface of the wall 18 to be narrowed significantly, such that in the preferred embodiment, the gap G between the two is under 10 millimeters, and can be as narrow as approximately 0.01 millimeters. This substantial reduction in the separation distance enhances the levitational stability, magnetic stiffness, and loading capacity of the bearing 14 without the concomitant cooling effects associated with prior art approaches for levitating magnetic bearings above cold superconducting elements.

In the illustrated embodiment, the cooling source 24 is a separate, substantially contained cooling chamber 26 holding a cryogen C, such as liquid nitrogen. The chamber 26 is defined by an outer wall 28 that is substantially thermally separated from the outer wall 18 of the cryostat 12 to minimize heat transfer. An inlet I is provided through this wall 28 for introducing the cryogen into the cooling chamber 26. To permit any vapor V to escape from the chamber 26 as the cryogen C warms, an exhaust outlet O is also provided (see action arrows in FIG. 1 also designating the inlet and outlet). In the illustrated embodiment, the inlet I and outlet O lines may be welded in place to suspend the cooling chamber 26 in the cryostat 12, but the use of any other support means that minimizes thermal transfer between the cooling chamber 26 and the cryostat wall or other housing 18 is also possible.

The rod 22 serving as the thermal link between the cooling source 24 and the superconducting element 20 is cylindrical and extends through the outer wall 28 of the cooling chamber 26. The entire surface area of the superconducting element 20 should contact the upper surface of the cylindrical rod 22 to ensure that thermal transfer is maximized. The rod 22 is preferably formed of materials having low thermal resistance/high thermal conductance, such as brass, copper, or aluminum.

As should be appreciated from viewing FIG. 1, and as previously noted, the combination of the outer wall 18 and the inner cooling chamber 26 in this first embodiment defines the chamber 25 around the superconducting element 20. Preferably, this chamber 25 is evacuated to minimize heat transfer from the cooling chamber walls 28 and the superconducting element 20 to the outer wall 18 of the cryostat 12. The evacuation pressure is preferably at least $10^{-3}$ torr, and most preferably on the order of $10^{-5}$ torr, but of course may be varied depending upon the requirements of a particular application. The important factor is that thermal transfer from the cooling source 24, which in this case is the cooling chamber 26 holding a cryogen C, and the superconducting element 20 to the outer wall 18 is minimized to avoid cooling the vessel 16 or fluid F held therein. Although a vacuum chamber 25 is presently proposed as one preferred manner of minimizing this thermal transfer, the use of other means to provide the desired thermal isolation is possible, such as by placing insulating materials or the like in the chamber 25.

As is known in the art, by cooling the superconducting element 20 in the presence of a magnetic field, it becomes capable of distributing the current induced by a permanent magnet such that the magnet levitates a certain distance above the superconducting element, depending primarily upon the intensity and the direction of the magnetic field generated by the levitating magnet. Although basically a repulsive force is created, the peculiar nature of the pinning forces generated actually tie the levitating magnet to the superconducting element as if the two were connected by an invisible spring. As should be appreciated, this form of attachment cannot be achieved in conventional levitation schemes for magnetic bearings that employ two opposed permanent magnets, since no pinning forces act to tie the two magnets together, while at the same time a balancing repulsive force is provided.

In the preferred embodiment of the present system 10, the element 20 providing the super conductive effects is a "high temperature type II" superconductor. Most preferably, the superconducting element 20 is formed of a relatively thin cylindrical pellet of melt-textured Yttrium-Barium Copper Oxide that, upon being cooled to a temperature of approximately 77–78 Kelvin using a cooling source 24, such as the illustrated liquid nitrogen chamber 26, exhibits the desired levitational properties in a permanent magnet. Of course, the use of other known superconducting materials having higher or lower operating temperatures is also possible, and my prior U.S. Pat. No. 5,567,672 is incorporated herein by reference for, among other things, the other high-temperature superconducting materials referenced therein.

The magnetic bearing 14 in the preferred embodiment includes a first permanent magnet 32 for positioning in the vessel 16 adjacent to the superconducting element 20 such that it levitates in the fluid F. Although the polarity of this first magnet 32 is not critical to creating the desired levitation, the magnet 32 is preferably disc-shaped and polarized in the vertical direction. This ensures that a symmetrical magnetic field is created by the magnet 32 and stable levitation results above the superconducting element 20 while free rotation relative to the vertical axis is possible.

In a version of the magnetic bearing 14 particularly adapted for use in relatively deep fluid vessels, a support shaft 34 is connected to and extends vertically from the first permanent magnet 32. Along the shaft 34, at least one, and preferably two, impellers 36 are carried that serve to provide the desired pumping, or in the case of FIG. 1, mixing action when the magnetic bearing 14 is rotated. Rotation of the levitating magnetic bearing 14 in the vessel 16 is achieved by a magnetic coupling formed between a second permanent magnet 38 (shown in dashed line outline in FIG. 1, but see also FIG. 2) and a drive magnet 40 positioned externally of the vessel 16. The drive magnet 40 is rotated by a drive means, such as an electric motor 42 or the like, and the magnetic coupling formed with the second permanent magnet 38 serves to transmit the driving torque to the bearing 14 to provide the desired pumping or mixing action. The direction of rotation is indicated by the action arrows shown in FIGS. 1 and 2 as being in the counterclockwise direction, but it should be appreciated that this direction is easily reversed by simply reversing the direction in which the drive magnet 40 is rotated.

In operation, and in practicing the method of pumping or mixing a fluid disclosed herein, the vessel 16 containing the fluid F and magnetic bearing 14 are together placed external to the wall 18 of the cryostat 12 adjacent to the superconducting element 20, which is placed in the chamber 25. When the first disc-shaped permanent magnet 32 is brought into the proximity of the superconducting element 20, the symmetrical magnetic field generated thereby causes the entire bearing 14 to levitate in a stable fashion above the bottom wall of the vessel 16. This levitation brings the second permanent magnet 38 into engagement with the drive magnet 40 to form the desired magnetic coupling. In addition to transmitting the driving torque, this magnetic coupling also serves to stabilize rotation of the magnetic bearing 14. The motor 42 or other motive device is then engaged to cause the drive magnet 40 to rotate, which in turn induces a steady, stable rotation in the bearing 14. Rotating impellers 36 then serve to mix or pump the fluid F in a gentle, yet thorough fashion.

Since the bearing 14 fully levitates and can be completely submerged in the fluid, the need for mixing or stirring rods penetrating through the vessel 16 is eliminated. The concomitant need for dynamic shaft seals or support bearings in the vessel walls is also eliminated. A related advantage is that the vessel 16 containing the fluid F and the magnetic bearing 14 can be completely sealed from the outside environment before mixing to provide further assurances against leakage or contamination. Yet another related advantage discussed in detail below is that the vessel 16 and magnetic bearing 14 can be formed of relatively inexpensive, disposable materials and simply discarded once mixing is complete. As should be appreciated, this advantageously eliminates the need for cleanup and sterilization of the magnetic bearing 14 and vessel 16. Thus, by completely sealing a disposable vessel containing a magnetic bearing and a fluid prior to mixing, the entire assembly can simply be discarded once the fluid contents are recovered, thereby reducing the risk of human exposure both during and after mixing in the case of hazardous fluids.

A second embodiment of the system 10 of the present invention particularly adapted for pumping a fluid F is shown in FIG. 2. In this embodiment, the vessel 16 includes at least one fluid inlet 44 and at least one outlet 46. The rotating impellers 36 serve to provide the desired pumping action by forcing fluid F from the inlet 44 to the outlet 46 (see action arrows). By increasing or decreasing the rotational speed of the motor 42 or other motive device, or adjusting the size, shape or style of the impeller blades, or substituting a different design altogether, a precise level of pumping action may be provided.

Another possible modification shown in FIG. 2 is to use a refrigerator 48 to provide the necessary cooling for the superconducting element 20 instead of a cryostat with a liquid cryogen. The refrigerator 48 can be positioned externally to a housing 18 containing the superconducting element 20, which may be the equivalent of the cryostat outer wall 18 previously described. As with the first embodiment, a chamber 25 is defined by the housing 18. This chamber 25 is preferably evacuated or filled with other insulating materials to minimize thermal transfer from the superconducting element 20 to the housing 18. However, since no cooling source 24 is contained within the housing 18, it is not actually a "cryostat" as that term is commonly defined. Nevertheless, the desired dual levels of thermal separation are still possible, and the concomitant advantages provided, since: (1) the cooling source 24, 48 is positioned away from the housing 18 and, thus, the vessel 16, magnetic bearing 14, and fluid F; and (2) the housing 18 still separates and defines a chamber 25 that thermally isolates the superconducting element 20 and the vessel 16. In yet another alternate arrangement, a refrigerator 48 can be used as a primary cooling source, with the cryogenic chamber 26 provided as a secondary or "backup" cooling source in the event of a power outage or mechanical failure (see, e.g., FIG. 2, which shows this feature in combination with a pumping vessel rather than a mixing vessel for purposes of illustration only).

In accordance with another of the many important aspects of the present system 10, the absence of a mixing rod or other mechanical stirrer extending through a wall of the vessel 16 also allows for placement of the magnetic bearing 14 at an off-axis position, as shown in FIG. 3. Specifically, the superconducting element 20, magnetic bearing 14, and drive magnet 40 are all axially aligned away from the vertical center axis of the vessel 16. One particular advantage of using this approach is that the magnetic bearing 14 may be rotated at a very low speed while the vessel 16 is also rotated about its center axis. This advantageously ensures that gentle, yet thorough mixing, is achieved, which is particularly advantageous for use with fluids that are sensitive to shear stress. As should be appreciated, this arrangement can be used both whether the vessel 16 is completely sealed, provided with an inlet 44 and an outlet 46 for pumping as shown in FIG. 2, or open to the ambient environment. For purposes of illustration only, FIG. 3 shows the cryostat 12 of the embodiment shown in FIG. 1 having an outer wall 18 and a cooling chamber 26 defined by a wall 28. However, it should be appreciated that use of the housing 18 and closed-cycle refrigerator 48 of the second embodiment of FIG. 2 as the "cryostat" is also possible with this arrangement.

Through experimentation, it has been discovered that when the magnetic bearing 14 of the type described for use in the preferred embodiment is employed, providing the requisite degree of stability to ensure that all contact with the side walls of the container 16 is avoided can be a concern. Thus, to ensure that the magnetic bearing 14 rotates with exceptional stability and such contact is completely avoided, the second permanent magnet 38 and the drive magnet 40 are each provided with at least two pair, and preferably four pair of cooperating sub-magnets 50a, 50b. As shown in FIGS. 4a and 4b, these magnets 50a, 50b preferably have opposite polarities and thereby serve to attract each other and prevent the levitating magnetic bearing 14 from making any substantial side-to-side movement. However, the attractive force is counterbalanced by the combined springlike attractive and repulsive levitational forces created between the first permanent magnet 32 and the superconducting element 20 when cooled. This avoids the potential for contact with the upper wall of the vessel 16, if present. Overall, the magnetic bearing 14 is capable of exceptionally stable rotation using this arrangement, which further guards against the undesirable frictional heating or shear stress created if the rotating bearing 14, or more particularly, the first and second permanent magnets 32, 38 or the blades of the impeller(s) 36 could move into close proximity with the bottom or side walls of the vessel 16.

As previously mentioned, one of the many advantages of the system 10 of the present invention is that, since the magnetic bearing 14 levitates in the fluid F and no mixing or stirring rods are required for rotation, the vessel 16 can be completely sealed from the outside ambient environment. Thus, by forming the bearing 14 and vessel 16 of relatively inexpensive or disposable materials, both can simply be discarded after mixing is completed and the fluid F is recovered. Of course, such disposable materials can also be used to form the vessel 16 designed for pumping fluids (FIG. 2), or to form the open-top container for mixing fluids, to avoid the need for clean up or sterilization once the operation is complete.

It should also be appreciated that the magnetic bearing 14 illustrated is a preferred arrangement only, and that other possible configurations are possible. For instance, impeller blades could simply be placed circumferentially around the disc-shaped first permanent magnet 32 to reduce the length of the shaft 34, or eliminate it altogether, if the vessel 16 is relatively short in the vertical dimension. Instead of a bladed impeller 36, the use of other structural arrangements is also possible, such as disc-shaped wheels having vanes or like structures designed to create the desired mixing or pumping action when rotated. Depending on the depth of the vessel 16, the length of the shaft 34, if present, can also be increased or decreased as necessary. All components forming the magnetic bearing in any embodiment described above may be coated with TEFLON or other inert materials to reduce the chances of contamination or corrosion, as well as to facilitate clean up, if required.

Of course, besides use in the mixing or pumping of small batches of fluid solutions or suspensions used during experimentation and research in the laboratory setting, all components are also easily scaled up for use in industrial or commercial pumping or mixing operations, such as those commonly used in the manufacture of pharmaceuticals on a large-scale basis. The levitation of the magnetic bearing can still be readily achieved in systems of much greater capacity than the one shown for purposes of illustration in the drawings, thus making the present arrangement particularly well-suited for the commercial production of pharmaceuticals or any other solutions or suspensions that require gentle, yet thorough mixing during processing.

Experiments conducted to date have demonstrated the efficacy of the system 10 described above as the most preferred embodiment. The set-up utilized in conducting these experiments included a magnetic bearing having axially aligned upper and lower magnets and an impeller mounted on a vertically extending support shaft, as shown in FIG. 1. A cylindrical pellet of melt-textured $YBa_2Cu_3O_{7+x}$ having a diameter of 30 millimeters and a thickness of 25 millimeters was used as the superconducting element and placed in a cryostat having a configuration similar to the one shown in FIG. 1. The cryostat included a cooling chamber filled with approximately 1 liter of liquid nitrogen. A Nd—Fe—B permanent magnet with a surface field intensity of 0.4 Tesla was used as the lower, first permanent magnet.

Experiments conducted using this set-up demonstrated that the desired exceptionally stable levitation of the magnetic bearing above the top surface of the cryostat in a vessel filled with a relatively warm fluid was possible. A separation distance of up to seven millimeters was achieved, and the levitation was stable for up to five hours using just a liter of liquid nitrogen as the cryogen. In the first experiment using this set up, water was selected as a model low viscosity fluid. Rotational speeds of up to 600 rpm were achieved—this upper limit being defined by only the limited capabilities of the motor used to rotate the drive magnet in this experiment. No decoupling or instability in the magnetic bearing was observed at any speed. In the case of glycerin, a model high viscosity fluid, a maximum rotational speed of 60 rpm was achieved before some decoupling of the magnetic bearing was observed. To further demonstrate the mixing capabilities using the proposed system, SEPHADEX powder (dry bead, 50–150 micron diameter) was placed on the bottom of a water-filled vessel and the levitating magnetic bearing rotated. A uniform suspension was achieved after approximately five minutes of mixing.

In summary, a system 10 using cold superconducting technology that is capable of pumping or mixing a relatively warm or otherwise temperature sensitive fluid using a levitating magnetic bearing 14 is disclosed. The magnetic bearing 14 carries at least one impeller 36 and is placed in a fluid vessel 16 positioned external to a cryostat 12 having an outer wall or other housing 18 for containing a superconducting element 20. A cooling source 24 (either a cryogenic chamber 26, FIGS. 1 and 3 or a refrigerator, FIG. 2) thermally linked to the superconducting element 20 provides the necessary cooling to create the desired superconductive effects and induce levitation in the magnetic bearing 14. Since the bearing levitates in the fluid F, no penetration of the vessel walls by mixing or stirring rods is necessary, which eliminates the need for dynamic bearings or seals. Additionally, the outer wall 18 of the cryostat 12 or other housing defines a chamber 25 that thermally isolates and separates the superconducting element 20 from the vessel 16 containing the fluid F and magnetic bearing 14. The thermal isolation may be provided by evacuating the chamber 25, or filling it with an insulating material. By virtue of this thermal isolation and separation, the superconducting element 20 can be positioned in close proximity to the outer wall or housing 18 adjacent to the vessel 16 and magnetic bearing 14, thereby achieving a significant reduction in the separation distance or gap G between the magnetic bearing 14 and the superconducting element 20. This enhances the magnetic stiffness and loading capacity of the magnetic levitating bearing 14, thus making it suitable for use with viscous fluids or relatively large volumes of fluid. The exceptionally stable levitation provided as a result of the reduced separation distance also significantly reduces the potential for contact between the rotating bearing and the bottom or sidewalls of the vessel, which makes this arrangement particularly well-suited for use in fluids that are sensitive to shear stress or the effects of frictional heating. However, since the superconducting element 20 is substantially thermally isolated and separated from the vessel 16, the magnetic bearing 14, and hence the fluid F contained therein, are not exposed to the cold temperatures generated by the cooling source 24 to produce the desired superconductive effects and the resultant levitation. This allows for temperature sensitive fluids to be mixed or pumped. By using means external to the vessel 16 to rotate and/or stabilize the magnetic bearing 14 levitating in the fluid F, such as a rotating drive magnet 40 magnetically coupled to the magnetic bearing 14, the desired pumping or mixing action is provided.

The foregoing description of a preferred embodiment of the present invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. An apparatus for the intended use of levitating a magnetic element, comprising:

a superconducting element capable of being placed in a superconducting state in accordance with a field cooling protocol and levitating the magnetic element;

a structure including a wall defining a first chamber in which the superconducting element is positioned, said first chamber thermally isolating the superconducting element from the wall; and a cooling source thermally linked to the superconducting element, wherein a gap is provided between said superconducting element and an inner surface of said wall of approximately 0.01 to 5 millimeters.

2. The apparatus according to claim 1, wherein the first chamber is evacuated or insulated to minimize thermal transfer to the wall and provide the desired thermal isolation.

3. The apparatus according to claim 2, wherein the first chamber is evacuated to a vacuum pressure of at least $10^{-3}$ torr.

4. The apparatus according to claim 1, wherein said superconducting element is a high temperature superconducting element.

5. The apparatus according to claim 1, wherein by way of the thermal link, said cooling source maintains the superconducting element at a temperature of between 4.2 to 130 Kelvin.

6. The apparatus according to claim 1, wherein the structure is a cryostat, said wall is the outer wall of the cryostat, a second chamber is positioned within the wall defining said first chamber, and said cooling source is a liquid cryogen in the second chamber.

7. The apparatus according to claim 1, wherein the cooling source is a liquid cryogen and further including a refrigerator capable of maintaining the superconducting element in a superconducting state, whereby the refrigerator serves as a primary cooling source and the liquid cryogen is a back-up or reserve cooling source.

8. An apparatus for the intended use of levitating a magnetic element, comprising:
a superconducting element capable of being placed in a superconducting state in accordance with a field cooling protocol;
a structure including a wall defining a chamber in which the superconducting element is positioned, said chamber thermally isolating the superconducting element from the wall; and
a refrigerator thermally linked to the superconducting element.

9. The apparatus according to claim 8, wherein the chamber is evacuated or insulated to minimize thermal transfer to said wall and provide the desired thermal isolation.

10. The apparatus according to claim 9, wherein the chamber is evacuated to a vacuum pressure of at least $10^{-3}$ torr.

11. The apparatus according to claim 8, wherein said superconducting element is a high temperature superconducting element.

12. The apparatus according to claim 8, wherein said refrigerator maintains the superconducting element at a temperature of between 4.2 to 130 Kelvin.

13. The apparatus according to claim 9, wherein the thermal linking is provided by a rod extending between the superconducting element and said refrigerator.

14. The apparatus according to claim 13, wherein said rod includes an engagement surface that is in contact with the entire area of an adjacent surface of the superconducting element to maximize thermal transfer.

15. The apparatus according to claim 8, wherein a gap is provided between the superconducting element and an inner surface of said wall of approximately 0.01 to 5 millimeters.

16. The apparatus according to claim 8, further including a second structure capable of holding a liquid cryogen in contact with the thermal link, whereby the second structure containing the liquid cryogen may serve as a backup or reserve cooling source for the superconducting element.

17. The apparatus according to claim 8, wherein the refrigerator is a closed-cycle refrigerator.

18. An apparatus for supplying a levitating force for a magnetic element, in a fluid-containing vessel, comprising:
a superconducting element capable of being placed in a superconducting state in accordance with a field cooling protocol and levitating the magnetic element;
a stable support structure for the vessel, said structure including a wall defining a first chamber in which the superconducting element is positioned, said first chamber being evacuated or insulated for thermally isolating the superconducting element from the wall;
a cooling source selected from the group consisting of: (a) a liquid cryogen held in second chamber in the structure; and (b) a refrigerator; and
a link for thermally linking said superconducting element to said cooling source.

19. The apparatus according to claim 18, wherein the link is a rod extending between the cooling source and the superconducting element, said rod having an engagement surface that is in contact with the entire area of an adjacent surface of the superconducting element to maximize thermal transfer.

20. The apparatus according to claim 18, wherein the refrigerator is a closed-cycle refrigerator.

21. The apparatus according to claim 18, including both the second chamber holding the liquid cryogen and the refrigerator.

22. A method for levitating a rotatable magnetic pumping or mixing element held in a vessel capable of receiving or holding a fluid using the apparatus of claim 18.

23. An apparatus for the intended use of levitating a magnetic element, comprising:
a superconducting element capable of being placed in a superconducting state in accordance with a field cooling protocol and levitating the magnetic element;
a structure including a wall defining a first chamber in which the superconducting element is positioned, said first chamber thermally isolating the superconducting element from the wall;
a cooling source; and
a rod extending between the superconducting element and the cooling source, said rod including an engagement surface contacting the entire area of an adjacent surface of the superconducting element to maximize thermal transfer.

24. A levitation apparatus, comprising:
a superconducting element capable of being placed in a superconducting state in accordance with a field cooling protocol;
a structure including a wall defining a first chamber in which the superconducting element is positioned, said first chamber thermally isolating the superconducting element from the wall;
a cooling source thermally linked to the superconducting element; and
a magnetic element positioned adjacent the wall and levitated by said superconducting element.

* * * * *